United States Patent [19]

Edwards et al.

[11] Patent Number: 4,567,174
[45] Date of Patent: Jan. 28, 1986

[54] BIS(1-SUBSTITUTED BIGUANIDE) DERIVATIVES

[75] Inventors: Philip N. Edwards, Bramhall; Michael S. Large, Congleton, both of England

[73] Assignee: Imperial Chemical Industries PLC, London, England

[21] Appl. No.: 607,703

[22] Filed: May 7, 1984

[51] Int. Cl.$^4$ ............... C07D 403/12; A61K 31/445; A01N 43/40
[52] U.S. Cl. .................................. 514/210; 514/212; 514/237; 514/316; 514/408; 514/635; 564/234; 564/235; 564/236; 260/239 A; 260/239 B; 544/86; 544/402; 546/186; 548/518
[58] Field of Search ..................... 564/234, 235, 236; 260/239 B, 239 AR; 544/86, 402; 546/186; 548/518; 424/244, 248.56, 250, 207, 274, 326

[56] References Cited

U.S. PATENT DOCUMENTS

| | | | |
|---|---|---|---|
| 2,508,376 | 5/1950 | Crowther et al. | 564/234 |
| 3,152,811 | 10/1964 | Shapiro et al. | 564/235 |
| 3,272,863 | 9/1966 | Cutler et al. | 564/235 |
| 3,468,898 | 9/1969 | Cutler et al. | 564/236 |

FOREIGN PATENT DOCUMENTS

| | | | |
|---|---|---|---|
| 705838 | 3/1954 | United Kingdom | 564/234 |
| 1095902 | 12/1967 | United Kingdom | 564/239 |

*Primary Examiner*—Robert T. Bond
*Attorney, Agent, or Firm*—Cushman, Darby & Cushman

[57] ABSTRACT

A bis(1-substituted biguanide) derivative of the formula:

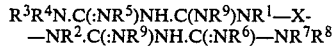

$$R^3R^4N.C(:NR^5)NH.C(NR^9)NR^1-X-NR^2.C(:NR^9)NH.C(:NR^6)-NR^7R^8 \quad V$$

or a tautomeric form thereof, wherein $R^1$, $R^2$ and $R^9$, which may be the same or different, are each hydrogen, a 1-16C alkyl radical, a 3-16C cycloalkyl radical, a (3-12C cycloalkyl)-(1-4C alkyl) radical, an optionally substituted phenyl or naphthyl radical, an optionally substituted phenyl(1-4C)alkyl or naphthyl(1-4C)alkyl radical or an optionally substituted diphenylmethyl radical, provided that at least one of $R^1$, $R^2$ and $R^9$ is other than hydrogen; $R^3$, $R^4$, $R^7$ and $R^8$, which may be the same or different are each hydrogen, or an alkyl, cycloalkyl, (cycloalkyl)alkyl, phenyl, naphthyl, phenylalkyl, naphthylalkyl, or diphenylmethyl radical as defined above, or a 2-16 alkoxyalkyl radical, or $R^3$, $R^4$ and the nitrogen atom to which they are attached, or $R^7$ and $R^8$ and the nitrogen atom to which they are attached, which may be the same or different, are each a 1-azetidinyl, 1-pyrrolidinyl, piperidino, hexamethyleneimino, heptamethyleneimino, morpholino or 4-(1-8C alkanoyl)-1-piperazinyl radical, each of which may bear 1-3C alkyl substituents; $R^5$ and $R^6$, which may be the same or different, are each hydrogen or a 1-8C alkyl radical; and X is a 2-16C linking group which is a straight chain alkylene radical, or a straight chain alkylene radical bearing one or more 1-16C alkyl substituents, of which any pair or pairs which are attached to different carbon atoms, may be joined so as to form, together with the intervening carbon atom or atoms of the alkylene radical, a (5-7C)-cycloalkyl radical or radicals; and the acid addition salts thereof, processes for their manufacture, and antibacterial and antifungal compositions and methods using said compounds.

8 Claims, No Drawings

BIS(1-SUBSTITUTED BIGUANIDE) DERIVATIVES

This invention relates to novel bis(1-substituted biguanides) which possess antibacterial properties.

Bis(5-substituted biguanide) derivatives are well known as antibacterial compounds. For example, in United Kingdom patent specification No. 705,838 there are disclosed and claimed bisbiguanides of the general formula:

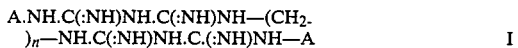

A.NH.C(:NH)NH.C(:NH)NH—(CH$_2$-)$_n$—NH.C(:NH)NH.C.(:NH)NH—A    I wherein A stands for a phenyl radical which is substituted by alkyl, alkoxy, nitro or halogen, and wherein the two A's may be the same or different, and wherein n is an integer from 2 to 9 inclusive, and wherein the polymethylene chain may be interrupted by oxygen atoms and/or by aromatic nuclei. The compounds are said to be useful as bactericides; for example, those of the formula:

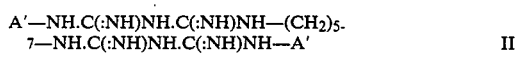

A'—NH.C(:NH)NH.C(:NH)NH—(CH$_2$)$_{5-7}$—NH.C(:NH)NH.C(:NH)NH—A'    II wherein A' stands for a halogen substituted phenyl radical possess very high antibacterial activity when tested in vitro against the organisms *Streptococcus haemolyticus, Staphylococcus aureus, Bacillus coli, Clostridium welchii* and *Pseudomonas pyocyanea*.

In United Kingdom patent specification No. 1,095,902 there is disclosed and claimed a broad group of bisguanides and bisbiguanides which includes inter alia compounds of the formula:

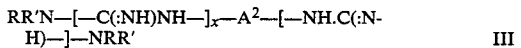

RR'N—[—C(:NH)NH—]$_x$—A$^2$—[—NH.C(:NH)—]—NRR'    III wherein A$^2$ stands for an alkylene radical of 2 to 12 carbon atoms having the valency bonds attached to different carbon atoms, or for a group of the formula:

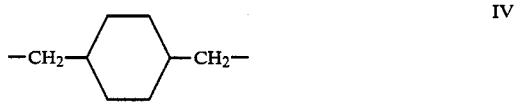

IV

R stands for an alkyl radical of 6 to 16 carbon atoms, R' stands for hydrogen, and x stands for 1 or 2. The bisguanides and bisbiguanides are said to have particular usefulness as plant fungicides and bactericides.

In contrast to the extensive literature on bis(5-substituted biguanides), typified by the patents discussed above, bis(1-substituted biguanides) are, so far as we can ascertain, totally unknown in the whole of the chemical literature, and thus constitute an entirely new class of antibacterial substances.

Thus, according to this invention there are provided bis(1-substituted biguanide) derivatives of the formula:

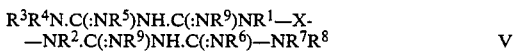

R$^3$R$^4$N.C(:NR$^5$)NH.C(:NR$^9$)NR$^1$—X—
—NR$^2$.C(:NR$^9$)NH.C(:NR$^6$)—NR$^7$R$^8$    V or a tautomeric form thereof, wherein R$^1$, R$^2$ and R$^9$, which may be the same or different, are each hydrogen, a 1–16C alkyl radical, a 3–16C cycloalkyl radical, a (3–12C cycloalkyl)-(1–4C alkyl) radical, an optionally substituted phenyl or naphthyl radical, an optionally substituted phenyl(1–4C)alkyl or naphthyl(1–4C)alkyl radical or an optionally substituted diphenylmethyl radical, provided that at least one of R$^1$, R$^2$ and R$^9$ is other than hydrogen; R$^3$, R$^4$, R$^7$ and R$^8$, which may be the same or different are each hydrogen, or an alkyl, cycloalkyl, (cycloalkyl)alkyl, phenyl, naphthyl, phenylalkyl, naphthylalkyl or diphenylmethyl radical as defined above, or a 2–16 alkoxyalkyl radical, or R$^3$, R$^4$ and the nitrogen atom to which they are attached, or R$^7$ and R$^8$ and the nitrogen atom to which they are attached, which may be the same or different, are each a 1-azetidinyl, 1-pyrrolidinyl, piperidino, hexamethyleneimino, heptamethyleneimino, morpholino or 4-(1–8C alkanoyl)-1-piperazinyl radical, each of which may bear 1–3C alkyl substituents; R$^5$ and R$^6$, which may be the same or different, are each hydrogen or a 1–8C alkyl radical, and X is a 2–16C linking group which is a straight chain alkylene radical, or a straight chain alkylene radical bearing one or more 1–16C alkyl substituents, of which any pair or pairs which are attached to different carbon atoms, may be joined so as to form, together with the intervening carbon atom or atoms of the alkylene radical, a (5–7C)-cycloalkyl radical or radicals; and the acid addition salts thereof.

Each of R$^1$, R$^2$, R$^3$, R$^4$, R$^7$ and R$^8$ may be, for example, a methyl, ethyl, n-propyl, isopropyl, n-butyl, isobutyl, sec-butyl, tert-butyl, pentyl, neopentyl, octyl, dodecyl, hexadecyl, cyclobutyl, cyclopentyl, cyclohexyl, cycloheptyl, cyclopentylmethyl or cyclohexylmethyl radical.

Each of R$^5$ and R$^6$ may be, for example, a methyl, ethyl, n-propyl, isopropyl, n-butyl, isobutyl, sec-butyl, tert-butyl, pentyl, neopentyl or octyl radical.

When any of R$^1$, R$^2$, R$^3$, R$^4$, R$^7$ and R$^8$ and R$^9$ are an optionally substituted phenylalkyl radical, it is preferably a benzyl, α-methylbenzyl, α-ethylbenzyl or phenethyl radical, and suitable optional substituents in the phenyl ring thereof, in the phenyl ring or rings of a naphthylalkyl (for example a naphthylmethyl) or diphenylmethyl radical, or in R$^1$, R$^2$, R$^3$, R$^4$, R$^7$, R$^8$ or R$^9$ when any of them is a phenyl or naphthyl radical are, for example, halogen atoms, for example chlorine, bromine, iodine or fluorine atoms, amino, carbamoyl, cyano, hydroxy, nitro and trifluoromethyl radicals, 1–6C alkyl, alkoxy, alkanoyl, alkylamino and alkanoylamino radicals and 2–6C alkoxycarbonyl and dialkylamino radicals. Suitable such radicals are, for example, methyl, ethyl, propyl, butyl, pentyl, hexyl, methoxy, ethoxy, propoxy, acetamido, propionamido, butyramido, methylamino, ethylamino, propylamino, acetyl, propionyl, butyryl, methoxycarbonyl, ethoxycarbonyl, dimethylamino and diethylamino radicals. Up to five such substituents may be present, but mono- and di-substituted phenyl rings are preferred, and especially mono-substituted rings.

Thus, further suitable values for R$^1$, R$^2$, R$^3$, R$^4$, R$^7$, R$^8$ and R$^9$ are, for example, 2-, 3- and 4-chlorophenyl, 2-, 3- and 4-bromophenyl, 2-, 3- and 4-fluorophenyl, 2,3-, 2,4-, 2,5-, 2,6-, 3,4- and 3,5-dichlorophenyl, 2-chloro-3-fluorophenyl, 2-, 3- and 4-methylphenyl, 2,3-, 2,4-, 2,5-, 2,6-, 3,4- and 3,5-dimethylphenyl, 2-, 3- and 4-methoxyphenyl, 2-, 3- and 4-acetylphenyl, 2-, 3- and 4-methylaminophenyl, 2-, 3- and 4-acetamidophenyl, 2-, 3- and 4-methoxycarbonylphenyl, 2-, 3- and 4-dimethylaminophenyl, 2-, 3- and 4-nitrophenyl, 2-, 3- and 4-chlorobenzyl, 2-, 3- and 4-bromobenzyl, 2-, 3- and 4-fluorobenzyl, 2,3-, 2,4-, 2,5-, 2,6-, 3,4- and 3,5-dichlorobenzyl, 2-chloro-4-fluorobenzyl, 2-, 3- and 4- methylbenzyl, 2,3-, 2,4-, 2,5-, 2,6-, 3,4- and 3,5-dimethylbenzyl, 2-, 3- and 4-methoxybenzyl, 2-, 3- and 4-acetylbenzyl, 2-, 3- and 4-methylaminobenzyl, 2-, 3- and 4-acetamidobenzyl, 2-, 3- and 4-methoxycarbonylbenzyl, 2-, 3- and 4-dimethylaminobenzyl, 2-, 3- and 4-nitrobenzyl, 2- , 3- and 4-chloro-α-methylbenzyl, 2-, 3- and 4-chlorophenethyl and bis(2-, 3- and 4-chlorophenyl)methyl radicals.

When one or more of $R^3$, $R^4$, $R^7$ and $R^8$, is an alkoxyalkyl radical, it may be, for example, a 2-methoxyethyl, 3-methoxypropyl, 3-hexyloxypropyl, 6-hexyloxyhexyl, 2-tetradecyloxyethyl or 15-methoxypentadecyl radical.

When $R^3$ and $R^4$, and $R^7$ and $R^8$, together with the nitrogen atom to which they are attached, form a heterocyclic radical, preferred such radicals are the 1-pyrrolidinyl and piperidino radicals.

Preferred values for $R^1$ and $R^2$ are methyl, isobutyl, decyl, dodecyl, hexadecyl, cyclohexyl, cyclododecyl, benzyl, 2-chlorobenxyl, 4-chlorobenzyl, 2,4- or 3,4-dichlorobenzyl and α-methylphenethyl radicals.

The linking group X may be, for example, a trimethylene, hexamethylene, heptamethylene, octamethylene, nonamethylene, decamethylene, undecamethylene, dodecamethylene, tetradecamethylene or hexadecamethylene radical. Suitable alkyl substituents on a straight chain alkylene radical X, are, for example, methyl, ethyl and n-propyl radicals, and a suitable value for X in which two pairs of such alkyl radicals are joined together is, for example, the methylenebis(4-cyclohexyl) diradical.

Preferred values for X are the trimethylene, hexamethylene, undecamethylene, dodecamethylene and methylene-bis(4-cyclohexyl) radicals.

The acid-addition salts of the invention may be derived from an inorganic or organic acid. In most circumstances it is preferable that the salts be derived from an acid which affords an anion which is suitable for human usage, for example a pharmaceutically acceptable anion. Examples of such acids are hydrochloric, hydrobromic, phosphoric, sulphuric, acetic, D-gluconic, 2-pyrrolidone-5-carboxylic, methanesulphonic, carbonic, lactic and glutamic acids.

Particular preferred compounds of the invention are dodecanebis(1-isobutyl-5-methylbiguanide), dodecanebis(5-ethyl-1-isobutylbiguanide), dodecanebis[1-isobutyl-3-(piperidinocarbonimidoyl)guanidine], 6-(5-ethylbiguanido)hexane(1-dodecyl-5-ethylbiguanide), 6-(5,5-dimethylbiguanido)hexane(1-dodecyl-5-methylbiguanide), dodecanebis(1-benzyl-5,5-dimethylbiguanide) and dodecanebis(5,5-diethyl-1-isobutylbiguanide), and their dihydrochlorides.

According to a further feature of the invention there is provided a process for the manufacture of the compounds of the invention wherein $R^5$ and $R^6$ are both hydrogen, which comprises reacting a bis-cyanoguanidine of the formula

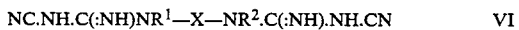

NC.NH.C(:NH)NR$^1$—X—NR$^2$.C(:NH).NH.CN  VI with an amine, $R^3R^4NH$, or with two different amines, $R^3R^4NH$ and $R^7R^8NH$ in the form of an acid-addition salt thereof, wherein X, $R^1$, $R^2$, $R^3$, $R^4$, $R^7$ and $R^8$ have the meanings stated above, at a temperature of 100° to 170° C.

A suitable amine salt is, for example, the hydrochloride. The reactants are heated together until the reaction is complete. The reaction proceeds fastest at higher temperature, but if thermal stability is a problem, the reaction should be carried out at a lower temperature over a longer period. The reactants are most conveniently melted together in the absence of a solvent, but if desired an inert solvent such as 2-methoxyethanol, 2-ethoxyethanol, nitrobenzene, sulpholane, isopropanol, n-butanol, ethylene glycol dimethyl ether or water, or a mixture of such solvents may be used.

The bis-cyanoguanidine of the formula VI, which may be used as the starting material in the above process, may be obtained by reacting the appropriate diamine $NH_2$—X—$NH_2$, in the form of an acid-addition salt, conveniently the dihydrochloride, with sodium dicyanamide, in conventional manner.

According to a further feature of the invention there is provided a process for the manufacture of the compounds of the invention of the formula V, which comprises reacting a diamine of the formula $R^1NH$—X—$NHR^2$, in the form of an acid-addition salt, with a cyanoguanidine of the formula:

$R^3R^4NH.C(:NR^5)NH.CN$   VII or with a cyanoguanidine of the formula VII and a cyanoguanidine of the formula:

$R^7R^8NH.C(:NR^6)NH.CN$   VIII wherein A, $R^1$, $R^2$, $R^3$, $R^4$, $R^5$, $R^6$, $R^7$ and $R^8$ have the meanings stated above, at a temperature of 100° to 170° C.

A suitable salt of the diamine is, for example, the dihydrochloride. The reactants are heated until the reaction is complete. The reaction proceeds fastest at higher temperature, but if thermal stability is a problem, the reaction should be carried out at lower temperature over a longer period. If a melt can be formed at those temperatures the reactants are conveniently melted together in the absence of a solvent. If not, or alternatively, the reactants are heated together in a suitable inert solvent, for example those mentioned above.

The amine of the formula $R^1NH$—X—$NHR^2$, which is used as the starting material in the above process, may be obtained by alkylation of the primary diamine $NH_2$—X—$NH_2$ in conventional manner, for example by reacting it with an alkyl halide, or by reductive alkylation with an aldehyde.

The cyanoguanidines of the formulae VII and VIII, wherein $R^5$ and $R^6$ are hydrogen, which are used as the starting materials in the above process, may be obtained by reacting sodium dicyanamide with an appropriate amine $R^3R^4NH$ or $R^7R^8NH$, in the form of an acid-addition salt, conveniently the dihydrochloride, in a suitable inert solvent.

The cyanoguanidines of the formulae VII and VIII wherein $R^5$ and $R^6$ are other than hydrogen, which may be used as starting materials in the above process, may be obtained by reacting a dialkyl (cyanoimido)dithiocarbonate, for example dimethyl (cyanoimido)dithiocarbonate, $(MeS)_2C:N.CN$, with appropriate amines $R^3R^4NH$ and $R^5NH_2$ (which are preferably the same), or $R^7R^8NH$ and $R^6NH_2$.

The acid-addition salts of the invention are obtained by conventional means.

The antibacterial activity of the compounds of the invention has been measured by the well-known minimum inhibitory concentration (MIC) test. Neat or diluted broth cultures of eight Gram positive organisms (Streptococcus pyrogenes, S. faecalis, 3 strains of Staphyloccus aureus, Listeria monocytogenes, Streptococcus mutans, S. sanguis), Candida albicans and fourteen Gram negative organisms (4 strains of Escherichia coli, Salmonella dublin, Klebsiella aerogenes, K. pneumoniae, E. cloacae, Serratia marcescens, Proteus vulgaris, P. mirabilis and 3 strains of Pseudomonas aeruginosa) were inoculated by means of an automatic microtitre inoculator on the surface of nutrient agar plates containing two-fold or five-fold dilutions of a test compound. After incubation overnight at 37° C., the MIC's of the test compound are read. The geometric mean MIC's for the eight Gram positive organisms and Candida, and 14 Gram negative organisms are then calculated for each test compound.

Depending upon its precise chemical structure, a compound of the invention has a mean MIC within the range 1–12 μg./ml. in agar against the 8 Gram positive organisms and Candida, and 20–250 μg./ml. in agar against the 14 Gram negative organisms.

The preferred compounds of the invention have an acute $LD_{50}$ within the accepted limits for compounds used topically, are of low irritancy in the Draize test on intact rabbit skin, are negative in the Ames test for mutagenicity, and are non-sensitizing in the Magnusson and Kligman contact sensitivity test in guinea-pigs.

Because of their antibacterial and antifungal properties the compounds of the invention are useful for many purposes, for example:

(a) in medical and veterinary practice for the disinfection of wounds, membranes and/or skin tissues; and (b) for the sterilisation of surgical instruments and other medical apparatus and equipment, for example respirators, ventilators, incubators, humidifiers, etc.;

(c) for incorporation in toothpastes and mouthwashes for inhibiting the formation of dental plaque, and gingivitis;

(d) for the disinfection of hard surfaces, for example plant and equipment used in the food and drink industries, and floors and walls in the home, factories and hospitals;

(e) for the disinfection of textiles, for example blankets, overalls, bed-linen, etc.;

(f) for the control of microbiological slime in the pulp and paper industries;

(g) for the control of micro-organisms in swimming pools, cooling water, pasteuriser water, aqueous oil emulsions such as metal working fluids, and other circulating water systems; and (h) and as plant bactericides and fungicides.

A drawback to the use of chlorhexidine is that if it contacts white textiles which are subsequently laundered with hypochlorite bleach, dark stains develop. It is an advantage of the preferred compounds of the present invention that such staining is non-existent, or minimal.

Compounds of the invention also possess useful antifungal activity against, for example, Candida albicans and Trichophyton mentagrophytes, and algicidal and antiyeast activity.

According to a further feature of the invention there are provided antibacterial or antifungal compositions comprising a compound of the formula V wherein $R^1$, $R^2$, $R^3$, $R^4$, $R^5$, $R^6$, $R^7$, $R^8$, $R^9$ and X have the meanings stated above, or an acid-addition salt thereof, and an inert diluent or carrier therefor.

The antibacterial or antifungal compositions of the invention are prepared by conventional means using conventional excipients. They include, for example, aqueous solutions, for example concentrated aqueous solutions, sterile, ready-to-use aqueous solutions, aqueous dispersions, and emulsions, for example oil-in-water emulsions, for example aqueous gels, creams, ointments and pastes. Suitable excipients include, for example, wetting agents, dispersing agents, emulsifying agents, gelling agents or thickening agents.

According to a further feature of the invention, there is provided a contraceptive method which comprises applying to sperm or the locus of sperm, a spermicidal, sperm-immobilising or mucospissic amount of a compound of the invention of the formula V.

In one aspect of this method, the compound of the formula V, when applied to vaginal mucus at a suitable concentration, very rapidly increases its viscosity, to the extent that it becomes essentially impenetrable to sperm, and forms a physical barrier to conception in the same way as a rubber sheath or a diaphragm cap.

Besides increasing the viscosity of vaginal mucus, when the mucus comes into contact with a bisbiguanide compound of the formula V, other changes occur in its intrinsic properties, such as its morphology, rheology and water uptake and visco-elastic properties, which can also effect its penetrability to sperm. The compounds also possess spermicidal or sperm-immobilising properties.

In vitro, the compounds of the formula V exert a useful contraceptive effect at concentrations down to about $10^{-3}$ to $10^{-4}\%$, and a suitable amount to be applied to the human vagina for contraceptive purposes is from 1.0 g. to $10^{-4}$ g.

The compound of the formula V may be applied to the vagina in conventional manner, for example as a pessary, cream, liquid douche, gel, aerosol foam or impregnated tampon, or in a controlled delivery device of the compound in a polymer matrix.

According to a further feature of the invention there is provided a compound of the formula V, or a composition thereof, for use as a contraceptive.

The invention is illustrated but not limited by the following Examples in which the temperatures ae expressed in degrees Celsius:

EXAMPLE 1

A mixture of 1,12-dodecanedi(2-chlorobenzylamine)-dihydrochloride (1.57 g.), dicyanidiamide (0.76 g.) and sulpholane (2 ml.) was stirred at 160⁻ (bath temperature) for 3 hours. The residue was cooled and dissolved in methanol (10 ml.), and the solution was added, with stirring, to acetone (200 ml.). The precipitated solid was collected and recrystallised from water to give 1,12-dodecanebis[1-(2-chlorobenzyl)biguanide]dihydrochloride, m.p. 227°–230°.

The 1,12-dodecanedi(2-chlorobenzylamine), used as starting material in the above process, may be manufactured as follows:

A mixture of dodecamethylene diamine (10 g.), 2-chlorobenzaldehyde (14.75 g.), ethanol (100 ml.), glacial acetic acid (10 ml.) and platinum IV oxide (0.4 g.) was shaken under hydrogen at room temperature and atmospheric pressure until 2.4 l. of hydrogen had been absorbed. The mixture was filtered, and the filtrate was treated with concentrated hydrochloric acid (10 ml.) and then evaporated to dryness. The residue was stirred with a mixture of water and ethyl acetate, and the insoluble solid was collected to give 1,12-dodecanedi(2-chlorobenzylamine)dihydrochloride m.p. 180°–184°.

EXAMPLES 2–66

The process described in Example 1 was repeated, using the appropriate substituted diamine and the appropriate optionally substituted dicyandiamide, to make the following compounds:

| | $R^3R^4N.C(:NR^5)NH.C(:NH)NR^1—(CH_2)_n—NR^2.C(:NH)—NH.C(:NR^6)NR^7R^8.2HCl$ | | | | |
|---|---|---|---|---|---|
| No. | $R^1(=R^2)$ | $R^3(=R^7)$ | $R^4(=R^8)$ | n | Crystallisation solvent | Melting point |
| 2 | 2-Cl benzyl | H | H | 11 | a | 184–186 (x) |
| 3 | 2-Cl benzyl | methyl | H | 11 | a | 127–129 (x) |
| 4 | 2-Cl benzyl | methyl | methyl | 11 | a | 190–192 (x) |
| 5 | 2-Cl benzyl | methyl | H | 12 | b | 140–143 |
| 6 | 2-Cl benzyl | ethyl | H | 12 | c | 95–105 |
| 7 | 2-Cl benzyl | methyl | methyl | 12 | a | 200–202 (x) |
| 8 | isobutyl | ethyl | H | 11 | gum | —(x) |
| 9 | isobutyl | isopropyl | H | 11 | gum | —(x) |
| 10 | isobutyl | isobutyl | H | 11 | a | 157–159 (x) |
| 11 | isobutyl | cyclohexyl | H | 11 | a | 164–166 (x) |
| 12 | isobutyl | methyl | methyl | 11 | a | 191–193 (x) |
| 13 | isobutyl | pentamethylene | | 11 | a | 187–188 (x) |
| 14 | isobutyl | H | H | 12 | d | 164–166 (x, y) |
| 15 | isobutyl | methyl | H | 12 | e | 122–125 (x, y) |
| 16 | cyclohexyl | H | H | 12 | a | 194–196 (x) |
| 17 | benzyl | H | H | 11 | a | 166–168 (x) |
| 18 | benzyl | methyl | H | 11 | a | 162 (x) 165 (x) |
| 19 | benzyl | ethyl | H | 11 | gum | —(x) |
| 20 | benzyl | isopropyl | H | 11 | gum | —(x) |
| 21 | benzyl | butyl | H | 11 | a | 120–123 (x) |
| 22 | benzyl | methyl | methyl | 11 | a | 195–200 (x) |
| 23 | benzyl | H | H | 12 | d | 183–185 |
| 24 | benzyl | methyl | H | 12 | c | 80–82 |
| 25 | benzyl | ethyl | H | 12 | gum | — |
| 26 | benzyl | methyl | methyl | 12 | c | 158–161 |
| 27 | benzyl | isopropyl | H | 12 | f | 131–134 |
| 28 | benzyl | H | H | 6 | g | 205–207 (y) |
| 29 | benzyl | methyl | H | 6 | c | 215–217 |
| 30 | benzyl | methyl | methyl | 6 | d | 215–216 (z) |
| 31 | benzyl | ethyl | H | 6 | b | 233 (y) |
| 32 | benzyl | isopropyl | H | 6 | b | 222–223 (z) |
| 33 | benzyl | isobutyl | H | 6 | c | 194–197 |
| 34 | benzyl | butyl | H | 6 | c | 186–188 |
| 35 | benzyl | hexyl | H | 6 | c | 179–181 |
| 36 | benzyl | cyclohexyl | H | 6 | h | 232–234 |
| 37 | benzyl | benzyl | H | 6 | c | 188–190 |
| 38 | 4-Cl benzyl | H | H | 6 | c | 222–225 |
| 39 | 4-Cl benzyl | methyl | H | 6 | c | 238–240 |
| 40 | 4-Cl benzyl | ethyl | H | 6 | c | 256–258 |
| 41 | 4-Cl benzyl | propyl | H | 6 | c | 234–236 |
| 42 | 4-Cl benzyl | butyl | H | 6 | c | 189–191 |
| 43 | 4-Cl benzyl | pentamethylene | | 6 | c | 222–223 |
| 44 | 2,4-Cl$_2$ benzyl | H | H | 6 | c | 228–230 |
| 45 | 2,4-Cl$_2$ benzyl | methyl | H | 6 | c | 222–224 |
| 46 | 2,4-Cl$_2$ benzyl | methyl | methyl | 6 | c | 235–236 |
| 47 | 2,4-Cl$_2$ benzyl | propyl | H | 6 | c | 224–226 |
| 48 | 2,4-Cl$_2$ benzyl | ethyl | ethyl | 6 | c | 236–238 |
| 49 | 3,4-Cl$_2$ benzyl | H | H | 6 | i | 212–215 |
| 50 | 3,4-Cl$_2$ benzyl | methyl | methyl | 6 | i | 215–217 |
| 51 | 3,4-Cl$_2$ benzyl | methyl | H | 6 | i | 231–233 |
| 52 | 3,4-Cl$_2$ benzyl | ethyl | H | 6 | i | 247–249 |
| 53 | 1-methyl-3-phenyl-propyl | H | H | 6 | a | 188–190 (x) |
| 54 | 1-methyl-3-phenyl-propyl | methyl | methyl | 6 | a | 189–191 (x) |
| 55 | 1-methyl-3-phenyl-propyl | ethyl | H | 6 | a | 188–189 (x) |
| 56 | 1-methyl-3-phenyl-propyl | isobutyl | H | 6 | a | 144–147 (x) |
| 57 | diphenyl-methyl | H | H | 6 | a | 167–172 (x) |
| 58 | diphenyl-methyl | methyl | H | 6 | a | 215–217 (x) |
| 59 | diphenyl-methyl | isopropyl | H | 6 | a | 231–232 (x) |
| 60 | diphenyl-methyl | methyl | methyl | 6 | a | 216–218 (x) |
| 61 | cyclo-dodecyl | H | H | 6 | a | 215–217 (x) |
| 62 | cyclo-dodecyl | methyl | H | 6 | a | 218–220 (x) |
| 63 | cyclo-dodecyl | isopropyl | H | 6 | j | 219–221 |
| 64 | isobutyl | isopropyl | H | 6 | a | 199–201 (x, y) |
| 65 | isobutyl | butyl | H | 6 | f | 170–171 |
| 66 | isobutyl | benzyl | H | 6 | k | 193–194 (y) | a - acetone
b - water
c - methanol/acetone
d - acetonitrile
e - isopropanol
f - methanol/acetonitrile
g - ethanol/acetonitrile
h - ethanol
i - ethanol/acetone
j - acetone/diethyl ether
k - acetone/bis(2-methoxyethyl)ether
x - purified by medium pressure liquid chromatography (MPLC) on Merck Lichoprep RP-18 eluting with a suitable methanol-water mixture
y - bis(2-methoxyethyl)ether, (diglyme), used as diluent in place of sulpholane
z - sulpholane omitted from the reaction mixture.

The 1,11-undecanedi(2-chlorobenzylamine) used as starting material for Examples 2–4 was manufactured as follows:

2-Chlorobenzaldehyde (9.84 g.) was added to a solution of 1,11-undecanediamine (5.58 g.) in ethanol (100 ml.) and the solution was kept at room temperature for 1 hour. The solution was warmed gently to redissolve the precipitated imine, and then stirred while adding sodium borohydride (2.38 g.) in portions over 1 hour. The reaction mixture was cautiously acidified to pH 1 with concentrated hydrochloric acid and then evaporated to dryness. The residue was stirred with a mixture of water and ether, and the insoluble solid was collected and recrystallied from water to give 1,11-undecanedi(2-chlorobenzylamine)dihydrochloride m.p. 201°–203°.

The 1,6-hexanedi(3,4-dichlorobenzylamine) used as starting material in Examples 49–52 was manufactured as follows:

A mixture of hexamethylene diamine (2.32 g.), potassium carbonate (5.56 g.), ethanol (20 ml.) and 3,4-dichlorobenzyl chloride (7.8 g.) was stirred at room temperature for 72 hours. The mixture was filtered and the filtrate was evaporated to dryness. The residue was stirred with a mixture of 2N aqueous hydrochloric acid and ether, and the insoluble solid was collected and recrystallised from ethanol to give 1,6-hexanedi(3,4-dichlorobenzylamine)dihydrochloride m.p. 265°–268°.

The 1,6-hexanebis(diphenylmethylamine) used as starting material in Examples 57–60 was manufactured as follows:

A mixture of hexamethylene diamine (2.32 g.), 1,8-diazabicyclo[5,4,0]undec-7-ene (6 g.), N,N-dimethylformamide (10 ml.) and diphenylmethyl chloride (10 g.) was heated at 90° for 1 hour and then cooled. The mixture was added to a stirred mixture of 1N hydrochloric acid and ethyl acetate and the insoluble solid was collected to give 1,6-hexanebis(diphenylmethylamine)dihydrochloride, m.p. 305°–308°.

The other α,ω-diamines used as starting materials in the above processes were manufactured by the process described in the second part of Example 1, using the appropriate diamine, and the appropriate aldehyde or ketone in place of 2-chlorobenzaldehyde, to give the following diamines:

| | | $R^1NH(CH_2)_nNHR^2 \cdot 2HCl$ | | | |
|---|---|---|---|---|---|
| $R^1(=R^2)$ | n | Carbonyl starting material | Catalyst | Crystallisation solvent | m.p. |
| 1-methyl-3-phenylpropyl | 6 | $Ph(CH_2)_2$—$COCH_3$ | $PtO_2$ | — | 202–205 |
| 4-Cl benzyl | 6 | 4-Cl benzaldehyde | $PtO_2$ | $EtOH/H_2O$ | 312–315 |
| 2,4-$Cl_2$ benzyl | 6 | 2,4-$Cl_2$ benzaldehyde | $PtO_2$ | EtOH | 249–252 |
| cyclododecyl | 6 | cyclododecanone | $PtO_2$ | $H_2O$ | 272–274 |
| isobutyl | 12 | isobutyraldehyde | 5% Pd/C | EtOH | 298 |
| isobutyl | 11 | isobutyraldehyde | 5% Pd/C | EtOH | 303–305 |
| cyclohexyl | 12 | cyclohexanone | 5% Pd/C | EtOH | 306–308 |
| benzyl | 12 | benzaldehyde | 5% Pd/C | $EtOH/H_2O$ | 280–282 |
| benzyl | 11 | benzaldehyde | 5% Pd/C | $EtOH/H_2O$ | 274–276 |

The 3-cyano-1-hexylguanidine used as starting material in Example 35 was manufactured as follows:

A mixture of hexylamine hydrochloride (63.5 g.), sodium dicyanamide (44.5 g.) and butanol (200 ml.) was heated under reflux for 18 hours and then cooled. The mixture was filtered and the filtrate was evaporated to dryness. The residue was stirred with water and the insoluble solid was collected and crystallised from aqueous ethanol to give 3-cyano-1-hexylguanidine m.p. 103°–105°.

EXAMPLE 67

A mixture of 1,12-dodecanedi(isobutylamine)dihydrochloride (0.96 g.), 3-cyano-1,1-dimethylguanidine (1.12 g.) and n-butanol (5 ml.) was heated at reflux for 24 hours. The mixture was cooled and then filtered, and the filtrate was evaporated to dryness. The residue was subjected to MPLC on reversed phase silica (Merck Lichoprep RP-18) using methanol-water (45:55) as eluant, and the eluate was monitored by a UV detector. Fractions containing the required bisbiguanide (UV absorption at 260 nm.) were combined and evaporated to dryness. The residue was triturated with acetone and the insoluble crystalline solid was collected to give 1,12-dodecanebis(1-isobutyl-5,5-dimethylbiguanide)-dihydrochloride, m.p. 199°–200°.

EXAMPLES 68–69

The process described in Example 67 was repeated, using the appropriate diamine and the appropriate substituted cyanoguanidine as starting materials, to provide the following compounds:

68—1,12-dodecanebis[N-isobutyl-N'-(piperidinocarbonimidoyl)amidine]dihydrochloride, m.p. 193–195−, crystallised from acetone after purification by MPLC on Merck Lichoprep RP-18 eluting with methanol-water.

69—1,12-dodecanebis(1-cyclohexyl-5,5-dimethylguanidine)dihydrochloride, m.p. 190°–192° after purification as for Example 68.

EXAMPLE 70

A mixture of 1,12-dodecanedi(isobutylamine)bismethane sulphonate (1.08 g.), 3-cyano-1-ethylguanidine (0.9 g.) and butanol (2 ml.) was stirred at 140° (bath temperature) for 4 hours in an open necked flask, allowing the butanol to evaporate. The crude reaction mixture was subjected to MPLC on reversed phase silica (Merck Lichoprep RP-18) using methanol-water (55:45) as eluant, and the eluate was monitored by a UV detector. Fractions containing the required bisbiguanide (UV maximum at 260 nm.) were combined and evaporated to dryness. The residue was triturated with acetone and the insoluble crystalline solid was collected, to give, 1,12-dodecanebis(5-ethyl-1-isobutylbiguanide)bismethanesulphonate m.p. 167°–168°.

EXAMPLES 71–76

The process described in Example 70 was repeated, using the appropriate diamine salt and the appropriate substituted dicyandiamide as starting materials, to give the following compounds:

71—1,11-undecanebis(5,5-diethyl-1-isobutylbiguanide)-dihydrochloride, m.p. 179°–181°, crystallised from ethanol-acetonitrile;

72—1,12-dodecanebis(5,5-diethyl-1-isobutylbiguanide)-dihydrochloride, m.p. 177°–179°, crystallised from ethanol-acetonitrile;

73—1,12-dodecanebis(1-cyclohexyl-5-methylbiguanide)dihydrochloride, m.p. 117–118−, crystallised from acetone after MPLC on Merck Lichoprep RP-18, eluting with methanol-water;

74—1,11-undecanebis(1-benzyl-5-ethylbiguanide)dimesylate, m.p. 183°–185°, crystallised from ethanol-acetonitrile;

75—1,12-dodecanebis(1-benzyl-5,5-diethylbiguanide)-dimesylate, m.p. 187°–189°, crystallised from ethanol-acetonitrile;

76—1,6-hexanebis(1-benzyl-5,5-dibutylbiguanide)dihydrochloride, m.p. 223°–224°, crystallised from acetone.

EXAMPLE 77

A mixture of ethylamine hydrochloride (1.32 g.) and 1-(3-cyanoguanidino)-3-(3-cyano-1-dodecylguanidino)-propane (1.6 g.) was fused at 145° for 4 hours. The reaction mixture was purified by MPLC, eluting with aqueous methanol, and the fractions containing bis-biguanide (UV absorption at 235 nm.) were combined and evaporated to dryness, to give 3-(1-dodecyl-5-ethylbiguanido)propyl(5-ethylbiguanide)dihydrochloride, m.p. 72°–76°.

The 1-(3-cyanoguanidino)-3-(3-cyano-1-dodecyl-guanidino)propane used as starting material in the above process may be manufactured as follows:

Dodecyl bromide (37.4 g.) was added dropwise to excess 1,3-propanediamine (111 g.) in methylene dichloride (100 ml.). During the addition the mixture was maintained at 5° with a cooling bath, then the mixture was stirred for 2 days. An aqueous solution of sodium hydroxide (0.165M, 500 ml.) was added to the reaction mixture, then methylene dichloride (500 ml.) was added and the organic layer was separated. The aqueous layer was extracted with methylene dichloride (2×250 ml.) again and all the methylene dichloride solutions were combined and washed with water (2×100 ml.). The organic layer was dried over anhydrous sodium sulphate and the solvent was evaporated under reduced pressure to give the produce as free base. This gum, which crystallised slowly on standing, was converted to 3-dodecylaminopropylamine dihydrochloride, m.p. >280° (d), by standard means.

3-Dodecylaminopropylamine dihydrochloride (15 g.) sodium dicyanamide (9.47 g.) and butanol (250 ml.) were heated under reflux for 4 hours. The mixture was allowed to cool, and filtered, and the solvent was evaporated under reduced pressure. The residue was suspended in toluene and evaporated to small volume under reduced pressure to yield a pale oil, which was purified by chromatography on silica gel, using a gradient elution of isopropanol/methylene dichloride starting at 1:9, and then eluting the required product using a ratio of 1:4. The product 1-(3-cyano-guanidino)-3-(3-cyano-1-dodecylguanidino)propane was obtained as a solid m.p. 126°–129°.

EXAMPLES 78–85

The process described in Example 77 was repeated, using the appropriate amine and bis(cyanoguanidine) starting materials, to prepare the following compounds:

| | $R^3R^4N.C(:NH)NH.C(:NR^9)NR^1.(CH_2)_n.NR^2.C—(:NR^9)NH.C(:NH)NR^7R^8.2HCl$ | | | | | | | | |
|---|---|---|---|---|---|---|---|---|---|
| Ex. | $R^1$ | $R^2$ | $R^3(=R^7)$ | $R^4(=R^8)$ | $R^9$ | n | Reaction time (hours) | Reaction temperature (°) | m.p. |
| 78 | dodecyl | H | methyl | methyl | H | 3 | 3 | 145 | 195–197 |
| 79 | hexadecyl | H | H | H | H | 3 | 6 | 150 | 215–221 |
| 80 | hexadecyl | H | methyl | H | H | 3 | 3.5 | 145 | 160–162 |
| 81 | hexadecyl | H | ethyl | H | H | 3 | 3.5 | 145 | 71–76 |
| 82 | hexadecyl | H | methyl | methyl | H | 3 | 3.5 | 145 | 186–188 |
| 83 | H | H | isopropyl | H | isobutyl | 6 | 3 | 160 | 230 |
| 84 | H | H | ethyl | H | isobutyl | 6 | 3 | 160 | 203–205 |
| 85 | H | H | isobutyl | H | isobutyl | 6 | 1.25 | 160 | 210–212 |

The unsymmetrically-substituted bis-cyanoguanidine used as starting material in Examples 79–82 was prepared by the process described in the latter part of Example 77, using hexadecylaminopropylamine dihydrochloride in place of dodecylaminopropylamine dihydrochloride; m.p. 149°–151°.

The 1,6-hexanebis(3-cyano-2-isobutylguanidine) used as starting material for Examples 83–85 was prepared as follows:

A solution of dimethyl(cyanoimido)dithiocarbonate (21.7 g.) in ethanol (250 ml.) was added slowly to a vigorously stirred solution of 1,6-hexanediamine (8.7 g.) in ethanol (500 ml.). A colourless precipitate formed rapidly and the reaction mixture was stirred overnight at room temperature. The product was filtered off, washed with ethanol and dried under vacuum to give 1,6-hexanebis(3-cyano-2-methylisothiourea), m.p. 218°. This material was used without further purification.

1,6-Hexanebis(3-cyano-2-methylisothiourea) (2 g.) was dissolved in dimethylsulphoxide (30 ml.) and excess isobutylamine (5.1 ml.) was added slowly, and the reaction mixture was stirred at room temperature over 65 hours. The product was precipitated from the reaction mixture by the addition of water, and filtered off, and the solid was recrystallised from aqueous ethanol to give 1,6-hexanebis(3-cyano-2-isobutylguanidine) m.p. 180°–182°.

EXAMPLES 86–92

The process described in Example 70 was repeated, using the appropriate diamine and the appropriate cyanoguanidine starting materials, to manufacture the following compounds:

| | $R^3R^4N.C(:NH)NH.C(:NR^9) NR^1(CH_2)_nNR^2.C(:NR^9)—NH.C(:NH)NR^7R^8.2HCl$ | | | | | | | | |
|---|---|---|---|---|---|---|---|---|---|
| Ex. | $R^1$ | $R^2$ | $R^3(=R^7)$ | $R^4(=R^8)$ | $R^9$ | n | Reaction time (hours) | Reaction temperature (°) | m.p. |
| 86 | methyl | methyl | 2-ethylhexyl | H | H | 6 | 3 | 145 | gum* |
| 87 | methyl | methyl | isobutyl | isobutyl | H | 6 | 2 | 160 | 222–223 |
| 88 | decyl | H | methyl | H | H | 6 | 3 | 145 | 56–57 |

-continued

R³R⁴N.C(:NH)NH.C(:NR⁹) NR¹(CH₂)ₙNR².C(:NR⁹)—NH.C(:NH)NR⁷R⁸.2HCl

| Ex. | R¹ | R² | R³(= R⁷) | R⁴(= R⁸) | R⁹ | n | Reaction time (hours) | Reaction temperature (°) | m.p. |
|---|---|---|---|---|---|---|---|---|---|
| 89 | dodecyl | H | H | H | H | 6 | 4 | 145 | 121–123 |
| 90 | dodecyl | H | methyl | H | H | 6 | 2 | 145 | 65–72 |
| 91 | dodecyl | H | ethyl | H | H | 6 | 4 | 145 | 134–136 |
| 92 | dodecyl | H | methyl | methyl | H | 6 | 4 | 145 | 162–164 |

*Characterised by fast atom bombardment mass spectrometry.

EXAMPLE 93

The process described in Example 70 was repeated at 160°, using 1,6-hexanebis(methylamine) and 3-cyano-1,2-di-isobutylguanidine as starting materials, to manufacture 1,6-hexanebis(4,5-di-isobutyl-1-methylbiguanide)dihydrochloride, a foam, characterised by fast atom bombardment mass spectrometry.

What we claim is:

1. A bis(1-substituted biguanide) derivative of the formula V:

R³R⁴N.C(:NR⁵)NH.C(:NR⁹)NR¹—X—
—NR².C(:NR⁹)NH.C(:NR⁶)—NR⁷R⁸ or a tautomeric form thereof, wherein R¹, R² and R⁹, which may be the same or different, are each hydrogen, a 1–16C alkyl radical, a 3–16C cycloalkyl radical, a (3–12C cycloalkyl)(1–4C alkyl) radical, a phenyl or naphthyl radical, a phenyl(1–4C) alkyl or naphthyl(1–4-C)alkyl radical or a diphenylmethyl radical, wherein said phenyl or naphthyl radical, said phenyl (1–4C) alkyl or naphthyl(1–4C)alkyl radical, or said diphenylmethyl radical may each include optional substituents selected from halogen atoms, amino, carbamoyl, cyano, hydroxy, nitro and trifluoromethyl radicals, 1–6C alkyl, alkoxy, alkanoyl, alkylamino and alkanoylamino radicals and 2–6C alkoxy-carbonyl and dialkylamino radicals, provided that at least one of R¹, R² and R⁹ is other than hydrogen; R³, R⁴, R⁷ and R⁸, which may be the same or different, are each hydrogen, or an alkyl, cycloalkyl, (cycloalkyl)alkyl, phenyl, naphthyl, phenylalkyl, naphthylalkyl, or diphenylmethyl radical as defined above, or a 2–16C alkoxyalkyl radical, or R³, R⁴ and the nitrogen atom to which they are attached, or R⁷ and R⁸ and the nitrogen atom to which they are attached, which may the same or different, are each a 1-azetidinyl, 1-pyrrolidinyl, piperidino, hexamethyleneimino, heptamethyleneimino, morpholino or 4-(1–8C alkanoyl)-1-piperazinyl radical, each of which may bear 1–3C alkyl substituents; R⁵ and R⁶, which may be the same or different, are each hydrogen or a 1–8C alkyl radical; and X is a 2–16C linking group which is a straight chain alkylene radical, or a straight chain alkylene radical bearing one or more 1–16C alkyl substituents, of which any pair or pairs which are attached to different carbon atoms, may be joined so as to form, together with the intervening carbon atom or atoms of the alkylene radical, a (5–7C)-cycloalkyl radical or radicals; and the acid addition salts thereof.

2. A compound as claimed in claim 1 wherein each of R¹, R², R³, R⁴, R⁷, R⁸ and R⁹, which may be the same or different, is hydrogen or a methyl, ethyl, n-propyl, isopropyl, n-butyl, isobutyl, sec-butyl, tert-butyl, pentyl, neopentyl, octyl, dodecyl, hexadecyl, cyclobutyl, cyclopentyl, cyclohexyl, cycloheptyl, cyclopentylmethyl, cyclohexylmethyl radical, or a phenyl, naphthyl, benzyl, α-methylbenzyl, α-ethylbenzyl, phenethyl, naphthylmethyl or diphenylmethyl radical each optionally substituted in a phenyl ring or rings thereof by chlorine, bromine, iodine or fluorine atoms, or by amino, carbamoyl, cyano, hydroxy, nitro, trifluoromethyl, methyl, ethyl, propyl, butyl, pentyl, hexyl, methoxy, ethoxy, propoxy, acetamido, propionamido, butyramido, methylamino, ethylamino, propylamino, acetyl, propionyl, butyryl, methoxycarbonyl, dimethylamino or diethylamino radicals; or each of R³, R⁴, R⁷ and R⁸ which may be the same or different, is a 2-methoxyethyl, 3-methoxypropyl, 3-hexyloxypropyl, 6-hexyloxyhexyl, 2-tetradecyloxyethyl or 15-methoxypentadecyl radical; or R³ and R⁴, or R⁷ and R⁸, together with the nitrogen atoms to which they are attached, which may be the same or different, form a 1-pyrrolidinyl or piperidino radical; each of R⁵ and R⁶ which may be the same or different, is hydrogen or a methyl, ethyl, n-propyl, isopropyl, n-butyl, isobutyl, sec-butyl, tert-butyl, pentyl, neopentyl or octyl radical; and X is a trimethylene, hexamethylene, heptamethylene, octamethylene, nonamethylene, decamethylene, undecamethylene, dodecamethylene, tetradecamethylene, hexadecamethylene or methylenebis(4-cyclohexyl) radical.

3. A compound as claimed in claim 2 wherein each of R¹, R², R³, R⁴, R⁷, R⁸ and R⁹, which may be the same or different, is a phenyl, naphthyl, benzyl, α-methylbenzyl, α-ethylbenzyl, phenethyl, naphthylmethyl, diphenylmethyl, 2-, 3- or 4-chlorophenyl, 2-, 3- or 4-bromophenyl, 2-, 3- or 4-fluorophenyl, 2,3-, 2,4-, 2,5-, 2,6-, 3,4- or 3,5-dichlorophenyl, 2-chloro-3-fluorophenyl, 2-, 3- or 4-methylphenyl, 2,3-, 2,4-, 2,5-, 2,6-, 3,4- or 3,5-dimethylphenyl, 2-, 3- or 4-methoxyphenyl, 2-, 3- or 4-acetylphenyl, 2-, 3- or 4-methylaminophenyl, 2-, 3- or 4-acetamidophenyl, 2-, 3- or 4-methoxycarbonylphenyl, 2-, 3- or 4-dimethylaminophenyl, 2-, 3- or 4-nitrophenyl, 2-, 3- or 4-chlorobenzyl, 2-, 3- or 4-bromobenzyl, 2-, 3- or 4-fluorobenzyl, 2,3-, 2,4-, 2,5-, 2,6-, 3,4- or 3,5-dichlorobenzyl, 2-chloro-4-fluorobenzyl, 2-, 3- or 4-methylbenzyl, 2,3-, 2,4-, 2,5-, 2,6-, 3,4- or 3,5-dimethylbenzyl, 2-, 3- or 4-methoxybenzyl, 2-, 3- or 4-acetylbenzyl, 2-, 3- or 4-methylaminobenzyl, 2-, 3- or 4-acetamidobenzyl, 2-, 3- or 4-methoxycarbonylbenzyl, 2-, 3- or 4-dimethylaminobenzyl, 2-, 3- or 4-nitrobenzyl, 2-, 3- or 4-chloromethylbenzyl, 2-, 3- or 4-chlorophenethyl or bis(2-, 3- or 4-chlorophenyl)methyl radical; and X is a trimethylene, hexamethylene, undecamethylene, dodecamethylene or methylenebis(4-cyclohexyl) radical.

4. A compound as claimed in claim 1 which is in the form of a salt with hydrochloric, hydrobromic, phosphoric, sulphuric, acetic, D-gluconic, 2-pyrrolidone-5-carboxylic, methanesulphonic, carbonic, lactic or glutamic acid.

5. A compound as claimed in claim 1 which is dodecanebis(1-isobutyl-5-methylbiguanide), dodecanebis(5-ethyl-1-isobutylbiguanide), dodecanebis[1-isobutyl-3-(piperidinocarbonimidoyl)guanidine], 6-(5-ethylbiguanido)hexane(1-dodecyl-5-ethylbiguanide), 6-(5,5-dimethylbiguanido)hexane(1-dodecyl-5-methylbiguanide), dodecanebis(1-benzyl-5,5-dimethylbiguanide) or dodecanebis(5,5-diethyl-1-isobutylbiguanide), or a dihydrochloride thereof.

6. An antibacterial or antifungal composition comprising an effective antibacterial or antifungal amount of a compound as claimed in claim 1 and an inert diluent or carrier therefor.

7. A method of obtaining an antibacterial or antifungal effect:
 (a) in medical and veterinary practice for the disinfection of wounds, membranes or skin tissue;
 (b) in the sterilisation of surgical instruments and other medical apparatus and equipment;
 (c) in toothpastes and mouthwashes for inhibiting gingivitis and the formation of dental plaque;
 (d) in the disinfection of hard surfaces;
 (e) in the disinfection of textiles;
 (f) in the control of microbiological slime in the plup and paper industries;
 (g) in the control of micro-organisms in swimming pools, cooling water, pasteuriser water, aqueous oil emulsions and other circulating water systems; or
 (h) against plant bacteria and/or fungi;
which comprises applying an antibacterially- or antifungally-effective amount of a bisbiguanide as claimed in claim 1 to the bacterially or fungally affected locus.

8. A contraceptive method which comprises applying to sperm, or the locus of sperm, a spermicidal, sperm-immobilising or mucospissic amount of a compound as claimed in claim 1.

* * * * *